United States Patent [19]

Blaser et al.

[11] 4,060,546
[45] Nov. 29, 1977

[54] PROCESS FOR THE MANUFACTURE OF ACYLATION PRODUCTS OF PHOSPHOROUS ACID

[75] Inventors: Bruno Blaser, Dusseldorf-Urdeibach; Hans-Günther Germscheid, Hosel; Karl-Heinz Worms, Dusseldorf, all of Germany

[73] Assignee: Henkel Kommanditgesellschaft auf Aktien, Dusseldorf-Holthausen, Germany

[21] Appl. No.: 869,437

[22] Filed: Sept. 25, 1969

Related U.S. Application Data

[63] Continuation of Ser. No. 703,789, Feb. 5, 1968, abandoned, which is a continuation of Ser. No. 446,742, March 8, 1965, abandoned, which is a continuation-in-part of Ser. No. 159,159, Dec. 13, 1961, abandoned.

[30] Foreign Application Priority Data

July 3, 1961    Germany .................................. 43035

[51] Int. Cl.$^2$ .............................................. C07F 9/38
[52] U.S. Cl. ............................................ 260/502.4 A
[58] Field of Search ................................ 260/502.4 A

[56] References Cited

FOREIGN PATENT DOCUMENTS 1,148,235  5/1963  Germany ........................ 260/502.4

OTHER PUBLICATIONS

Brooks, "J. Am. Chem. Soc.", vol. 34, (1912), pp. 492-499.
Beilstein, "Handbuch der Organischen Chemie", vol. 2, (1920), pp. 171-172.

Primary Examiner—Joseph E. Evans
Attorney, Agent, or Firm—Hammond & Littell

[57] ABSTRACT

A process for the manufacture of acylation products of a phosphorous acid having at least two phosphorus atoms in their molecules, which consists essentially of the steps of mixing one mol of phosphorus trichloride with from 2.5 to 3 mols of a mixture of carboxylic acid plus water, said acid being selected from the group consisting of an aliphatic monocarboxylic acid having 2 to 12 carbon atoms and benzoic acid; the share of said water in said mixture being from 1.2 to 1.5 mols; at a temperature up to 80° C; heating the reaction blend thus obtained, after completing of said mixing to 100° C to 160° C and recovering said acylation products.

10 Claims, No Drawings

PROCESS FOR THE MANUFACTURE OF ACYLATION PRODUCTS OF PHOSPHOROUS ACID

This application is a continuation of our copending application Ser. No. 703,789, filed Feb. 5, 1968, now abandoned, which application is a continuation of Ser. No. 446,742, filed Apr. 8, 1965, now abandoned, which application in turn is a continuation-in-part of our application Ser. No. 159,159, filed Dec. 13, 1961, now abandoned.

The invention relates to a novel process for the manufacture of acylation products of phosphorous acid and, more particularly, of such products having at least two phosphorus atoms in their molecules.

A number of processes are known according to which acetylation products of phosphorous acid can be produced. For instance, acetyl chloride can be reacted with phosphorous acid, if desired also in the presence of acetic anhydride. Another method, often employed in practice consists in the variation that, in lieu of reacting acetyl chloride with phosphorous acid, components are used as starting materials which react under formation of these materials, i.e., $PCl_3$ and anhydrous acetic acid can be used as starting materials, whereby these components, for reasons of stoichiometry, are employed in a ratio of 1:3. All these processes are carried out in the absence of water in the reaction mixture.

It now has been found feasible, without decreasing to any practical extent the yield of the acylation products of phosphorous acid having at least two phosphorus atoms in their molecules, to replace a part of the acetic acid hitherto employed with water. According to the invention, 1 mol phosphorus trichloride can be reacted with at least 2.5 mols, and preferably 3 mols, of carboxylic acid plus water, whereby the share of the water may amount to 0.6 mols or 1.2 to 1.5 mols as shown in Examples 1 to 6 of Ser. No. 159,159, up to 1.6 mols when monocarboxylic acids are used whose quantity is 1.4 to 2.4 mols. When, in lieu of the monocarboxylic acids, dicarboxylic acids are employed, the share of the water is 2.1 to 2.5 mols and that of the dicarboxylic acids 0.25 to 0.5 mols. In carrying out the reaction, it is advantageous to add $PCl_3$ with agitation slowly to a mixture of acetic acid and water. The reaction mixture, if required, is cooled during that addition in order to avoid overheating. However, it is also possible to reverse the process, i.e., to add the water plus acid to $PCl_3$. Finally, the phosphorus trichloride may also be mixed with the carboxylic acid, and water added thereto, or water and $PCl_3$ may be premixed and the acid added. The method named first, however, is generally preferred.

After a reaction between the starting materials has occurred, opportunely at temperatures of 0° C to 80° C, and preferably at temperatures of 15° C to 60° C, the reaction mixture is further heated to temperatures between 60° and 200° C, and preferably between 100° and 160° C and held at this temperature for 1 to 6 hours. Agitation can be applied if desired.

It furthermore has been found that the reaction described above using acetic acid can also be accomplished with other carboxylic acids, such as aliphatic monocarboxylic acids with 2–20 carbon atoms, aromatic monocarboxylic acids and polycarboxylic acids, especially dicarboxylic acids with 3–10 carbon atoms. Preferably such carboxylic acids as propionic acid, butyric acid, caproic acid, caprylic acid, capric acid, may be used and also acids having even longer carbon chains, such as lauric acid, further benzoic acid, malonic acid, succinic acid, glutaric acid, adipic acid, pimolic acid, suberic acid, azolaic acid, sebacic acid.

This shows that in the manner described not only acetylation products, but acylation products of phosphorous acid are obtained.

After the reaction has been accomplished, the excess of the acylation agent is separated, and the reaction product thus is refined. This separation usually can be carried out by distillation, preferably at reduced pressure. In the case of acetic acid, a partial distillation of acetyl chloride formed takes place during the heating to higher temperatures, as described above. The reaction product obtained can be employed either directly or, if required, after purification, for instance by recrystallization, or by other means known per se. A treatment with water under certain definite conditions, i.e., at temperatures above 60° C, has been found especially applicable.

It frequently is opportune to convert the acids obtained in the process according to the invention into their alkali salts. This is accomplished, for instance, by neutralization with alkali hydroxides in the presence of water or else with alcoholic alkali hydroxide solutions.

The acylation products or their alkali salts can be employed for the prevention of calcite precipitation in the dehardening process of water and also as stabilizers for percompounds.

The constitution of the acylation products of phosphorous acid produced by the process according to the invention has not fully been established. Investigations so far have shown that in the case of monocarboxylic acids compounds of the generic formula (1) form:

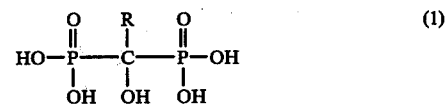

wherein R denotes an alkyl radical having one carbon atom less than the carboxylic acid employed in the reaction. However, it has been established in all instances that the compounds contain at least two phosphorus atoms in their molecules. It also has definitely been established that, when observing given reaction conditions, products of equal composition and of equal properties can be manufactured in a reproducible manner.

The partial replacement of the acylation agent with water yields the same product as obtained by employment of the acylation agent without water.

The phosphonic acids produced in the manner described have surface-active properties when they contain longer carbon chains and, hence, are suited as cleansing agents and detergents. Phosphonic acids produced with carboxylic acids having shorter carbon chains are good complex formers with polyvalent cations and effectively inhibit calcite formation in hard water, even in very small concentrations.

The invention now will be further explained by the following Examples. However, it should be understood that these are given merely by way of illustration, not of limitation, and that numerous changes may be made in the details without departing from the spirit and the scope of the invention.

EXAMPLE 1

1 mol $PCl_3$ was slowly added to the mixtures of acetic acid and water shown in Table 1 with steady agitation while holding the temperature below 50° C. After completed addition, the temperature was raised within 30 to 60 minutes to 110° – 120° C and stirring continued after attaining this temperature range for 1 hour. Water then was added to the reaction mixture, and the unreacted quantity of phosphorus determined by titration with iodine solution.

TABLE 1.

| Mixture | | Unreacted Phosphorus |
|---|---|---|
| Mols $CH_3COOH$ | Mols $H_2C$ | % |
| 0.6 | 2.4 | 45 |
| 1.2 | 1.8 | 18.4 |
| 1.4 | 1.6 | 4.15 |
| 1.5 | 1.5 | 2.25 |
| 1.6 | 1.4 | 1.8 |
| 2 | 1 | 1.6 |

Upon use of the acylating agents in the quantity corresponding to the formula of the products obtained, a reaction of less than 50 percent is obtained. Only if the water addition is held at a maximum of 1.6 mols per mol $PCl_3$, according to the invention, is an appreciable reaction of the phosphorus atoms in the molecule assured. When the share of the water is raised above 1.6 mols per mol $PCl_3$, the degree of reaction decreases considerably.

However, when the quantity of water is lowered to 0.6 mols per mol $PCl_3$, the reaction time for obtaining a complete reaction to the compounds according to the invention is lengthened considerably (see Example 2 below). Further reduction of the amount of water used renders the process unusable in practice owing to the greatly prolonged reaction times.

EXAMPLE 2

1 mol $PCl_3$ was slowly introduced with agitation into a mixture consisting of 0.6 mols water and 2.4 mols acetic acid. The reaction mixture then was heated, and 3 hours were required to raise it to 110° C. At this temperature, the mixture was stirred for one hour. The quantity of unreacted phosphorus was determined with iodine solution as 2.1 percent. When the temperature was not raised to 110° C, the reaction was incomplete. The mixture was diluted with 200 ml water, and the temperature again raised, this time to 140° C, by conducting steam into it. The solution thus obtained then was cooled, the crystallized acid suction-filtered and dried. The yield was 101 g or 90% of the theory.

EXAMPLE 3

To 1.8 mols acetic acid and 1.2 mols water, 1 mol $PCl_3$ was added gradually with agitation. The temperature then was increased within 2 hours to 120° C, and the mixture held at this temperature for another hour. The temperature then was raised to 140° C and steam blown into the reaction mixture until the distillate was practically free of acid. The product thus obtained was recrystallized from a little water. The yield was 103 g, or 92 percent of the theory, calculated on the phosphorus entered.

The acid crystallizes with one mol water of crystallization. The analytical values found are:

P, 27.40% found, 27.65 calculated;
C, 10.94% found, 10.72 calculated.

corresponding, also in its chemical properties, to the formula (2):

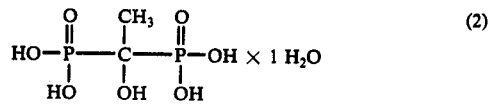

EXAMPLE 4

A mixture of 190 kg 90% acetic acid and 26 kg water was prepared, corresponding to a molar ratio of $CH_3COOH : H_2O$ of 1.6 : 1.4. To this mixture, 245 kg $PCl_3$ were added, whereby, after initial warming to 40° C, the mixture cooled. The temperature then was raised to 120° C with agitation, whereby a little acetyl chloride distilled, and held at this temperature for 1 hour. 150 liters water were then added to the viscous reaction mixture, and steam was blown into it at a temperature of 130° C. The mixture, while still pumpable, was neutralized with 50% aqueous NaOH in a mixing nozzle, whereby the reaction product solidified while cooling. It was comminuted by grinding. A 1 percent solution of this product had a pH of substantially 7. The yield was 298 kg or 94 percent of the theory, calculated on the phosphorus.

EXAMPLE 5

To 1.8 mols propionic acid and 1.2 mols water, 1 mol $PCl_3$ was added dropwise while cooling and stirring the mixture. Agitation was continued after all $PCl_3$ had been entered and the temperature raised to 130° C. The reaction mixture then was held at this temperature for 1 hour. Through the viscous mass thus obtained, steam was blown at the same temperature for 1 hour. The concentrated aqueous solution then was adjusted with 40% aqueous NaOH to a pH of 7, and the reaction product was precipitated in crystalline form by addition of a little methanol.

The yield was 155 g or 78.5 percent of the theory, calculated on the phosphorus.

EXAMPLE 6

3 mols caproic acid were mixed with 3 mols water, 2 mols $PCl_3$ were dropped into that mixture with agitation and external cooling. After the exothermic reaction had ceased, the mixture was heated to 140° C and stirred at this temperature for 3 hours. The reaction product then was subjected to the steam treatment as described in Example 5. The aqueous acid solution was adjusted to a pH of 7 with 40% aqueous NaOH solution, and, upon addition of a little methanol, the sodium salt precipitated in the form of well-shaped crystals. The yield was 240 g or 66.8 percent of the theory, calculated on the phosphorus.

EXAMPLE 7

2 mols $PCl_3$ were dropped within 30 minutes into a mixture of 3 mols lauric acid and 3 mols water. The mixture then was agitated and heated at 70°–80° C for 1 hour and then at 140° C for 3 hours. The volatile components then were removed by distillation in vacuo (3 mm Hg, 120° C). The residue was dissolved in ethanol, and the sodium salt precipitated with alcoholic HaOH.

The yield was 369 g or 80.5 percent of the theory.

EXAMPLE 8

1.5 mols benzoic acid were mixed with 1.5 mols water, and 1 mol $PCl_3$ dropped into the mixture. The latter then was heated at 130° C for 6 hours, and the reaction product subjected to a steam distillation until the distillate was free of acid. The residue was neutralized to a pH of 7 with 40% aqueous NaOH and precipitated by the addition of alcohol.

The yield was 118 g or 70 percent of the theory.

EXAMPLE 9

1.2 mols $PCl_3$ were dropped into 0.5 mols adipic acid which had been heated to 80° C. The mixture was stirred at that temperature for 1 hour. Two layers formed thereby. Then, 2.5 mols water were added while cooling externally with an ice-NaCl mixture. Thereafter, the reaction mixture was stirred at 160° C for 8 hours. The reaction product was dissolved in water, adjusted to a pH of 7 with 20% aqueous NaOH solution, and the end product precipitated with methanol.

The yield was 117 g or 57 percent of the theory.

EXAMPLE 10

2 mols $PCl_3$ were mixed with 0.5 mols glutaric acid and stirred for 30 minutes. 0.5 mols water then were added dropwise while cooling. The reaction mixture, after completed water addition, was agitated for 8 hours at 140°–150° C. After cooling, it was dissolved in water, and 340 ml 40% aqueous NaOH added. The salt thus formed was precipitated by the addition of ethanol, again dissolved in water, reprecipitated with methanol, suction-filtered and dried.

The yield was 220 g sodium salt containing water of crystallization corresponding to 56% of the theory, calculated on the phosphorus employed.

We claim:

1. A process for the manufacture of acylation products of a phosphorous acid having at least two phosphorus atoms in their molecules, which consists essentially of the steps of mixing one mol of phosphorus trichloride with from 2.5 to 3 mols of a mixture of carboxylic acid plus water, said acid being selected from the group consisting of an aliphatic monocarboxylic acid having 2 to 12 carbon atoms and benzoic acid; the share of said water in said mixture being from 1.2 to 1.5 mols; at a temperature up to 80° C; heating the reaction blend thus obtained, after completing of said mixing to 100° C to 160° C and recovering said acylation products.

2. The process as defined in claim 1, wherein said temperature of 100° C to 160° C is held for 1 to 6 hours.

3. The process as defined in claim 1 wherein said heated blend is allowed to cool, and the acylation product precipitated therefrom.

4. The process as defined in claim 1 wherein said trichloride is introduced into said mixture of acid and water.

5. The process as defined in claim 1, wherein said water is added into a mixture of said chloride with said acid.

6. A process for the manufacture of acylation products of a phosphorous acid having at least two phosphorus atoms in their molecules, which consists essentially of the steps of mixing one mol of phosphorus trichloride with from 2.5 to 3 mols of a mixture of carboxylic acid plus water, said acid being selected from the group consisting of an aliphatic monocarboxylic acid having 2 to 12 carbon atoms and benzoic acid; the share of said water in said mixture being from 1.2 to 1.6 mols; at a temperature up to 80° C; heating the reaction blend thus obtained, after completing of said mixing to 80° C to 200° C and recovering said acylation products.

7. The process as defined in claim 6, wherein said temperature of 80° C to 200° C is held for 1 to 5 hours.

8. The process as defined in claim 6 wherein said heated blend is allowed to cool, and the acylation product precipitated therefrom.

9. The process as defined in claim 6 wherein said trichloride is introduced into said mixture of acid and water.

10. The process as defined in claim 6, wherein said water is added into a mixture of said chloride with said acid.

* * * * *

UNITED STATES PATENT OFFICE
CERTIFICATE OF CORRECTION

Patent No. 4,060,546   Dated  Nov. 29, 1977

Inventor(s) Bruno Blaser et al.

It is certified that error appears in the above-identified patent and that said Letters Patent are hereby corrected as shown below:

Column 6, line 32, "5 hours" should read -- 6 hours --.

Signed and Sealed this

Thirtieth Day of May 1978

[SEAL]

Attest:

RUTH C. MASON  
Attesting Officer

LUTRELLE F. PARKER  
Acting Commissioner of Patents and Trademarks